United States Patent
Robledo

(10) Patent No.: US 9,265,782 B2
(45) Date of Patent: Feb. 23, 2016

(54) COMPOSITIONS, METHODS, AND DEVICES FOR THE TREATMENT OF EYE STAIN

(71) Applicant: Ader Enterprises, Inc., San Diego, CA (US)

(72) Inventor: Emilio Robledo, Tijuana (MX)

(73) Assignee: Ader Enterprises, Inc., San Diego, CA (US)

( * ) Notice: Subject to any disclaimer, the term of this patent is extended or adjusted under 35 U.S.C. 154(b) by 0 days.

(21) Appl. No.: 14/186,357

(22) Filed: Feb. 21, 2014

(65) Prior Publication Data

US 2014/0242176 A1 Aug. 28, 2014

Related U.S. Application Data

(60) Provisional application No. 61/768,284, filed on Feb. 22, 2013.

(51) Int. Cl.
*A61K 31/7048* (2006.01)
*A61K 9/00* (2006.01)

(52) U.S. Cl.
CPC .......... *A61K 31/7048* (2013.01); *A61K 9/0048* (2013.01)

(58) Field of Classification Search
CPC ................................................. A61K 9/0048
See application file for complete search history.

(56) References Cited

U.S. PATENT DOCUMENTS

| | | | | |
|---|---|---|---|---|
| 5,611,464 A | * | 3/1997 | Tsao et al. | 222/189.06 |
| 8,778,385 B1 | * | 7/2014 | Winkowski | 424/442 |
| 2005/0256081 A1 | * | 11/2005 | Peyman | 514/56 |

OTHER PUBLICATIONS

Abelson, M. "Demystifying demulcents", Review of Ophthalmology, Nov. 15, 2006 [printed on Jan. 9, 2015].*

* cited by examiner

*Primary Examiner* — Gina Justice
(74) *Attorney, Agent, or Firm* — Knobbe, Martens, Olson & Bear, LLP

(57) ABSTRACT

Embodiments provided herein relate to compositions, methods, and devices useful for treating eye stain. More particularly, compositions and devices are provided that include tylosin and a carrier suitable for ophthalmic application. Such compositions and devices can be used to treat eye stain in an animal, such as a dog or cat.

16 Claims, 7 Drawing Sheets

Schirmer Tear Test strip and procedure

Results

Insufficient tear production

Possible shortage of tears

Normal tear production

Before Application of Solution A  30 days after Application of Solution A

6A

6B

6C

6D

Before Application of Solution B

7A 30 days after Application of Solution B

7B

COMPOSITIONS, METHODS, AND DEVICES FOR THE TREATMENT OF EYE STAIN

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

Embodiments provided herein relate to compositions, methods, and devices useful in the field of medicine. More particularly, the embodiments provided herein are useful in the field of veterinary medicine for the treatment of stain, such as eye stain.

BACKGROUND

Many animals, especially dogs and cats, are afflicted with a condition known as "eye stain" or "tear stain," which is characterized by excessive discharge from the eyes that leaves an unsightly red or brown stain on the animal's hair. Such staining is especially pronounced in light-colored animals in which pigments in the tears can easily stain their hair.

Eye stain is thought to have a number of causes relating to excess tearing. The medical term chromodacryorrhea refers to an overproduction of tears with an excessive secretion of ferroporphyrins in tears, saliva, and urine. Ferroporphyrins have a characteristic red color and can cause eye stain particularly in light-colored animals. In mammals, ferroporphyrins are excreted primarily through bile and the intestinal tract. In dogs and cats ferroporphyrins are also excreted through tears, saliva and urine, and can stain hair in areas that come into contact with these bodily fluids.

Eye stain can also result from a variety of health, dietary, and genetic factors underlying excessive tearing. For instance, bacteria and yeast can grow on an animal's hair that is made moist and damp from excessive tearing. As a consequence, these bacteria and yeast grow in close proximity to the eyes and can cause infection of the eyes. Ptyrosporin, known as "red yeast," is thought to be associated with reddish-brown facial stains and can cause a foul odor in the affected areas. Additionally, some animals can have shallow eye sockets, eyelids turned inward so as to block tear drainage holes, hair growth around the eye that wicks tears onto the face, or eye damage in which scar tissue blocks tear drainage holes. As such, there are multiple causes of excessive tearing responsible for eye stain in animals.

SUMMARY OF THE INVENTION

Embodiments of the present invention relate to compositions, methods, and devices useful in the treatment of stain, such as eye stain. Certain embodiments relate to compositions comprising tylosin or a pharmaceutically acceptable salt thereof and a carrier suitable for ophthalmic application. In several aspects, the embodiments further comprise an ophthalmic demulcent.

In some embodiments of the compositions described herein, the pharmaceutically acceptable salt of tylosin is selected from the group consisting of tylosin acetate, tylosin adipate, tylosin aspartate, tylosin benzoate, tylosin besylate, tylosin bicarbonate or carbonate, tylosin bisulphate or sulphate, tylosin borate, tylosin camsylate, tylosin citrate, tylosin cyclamate, tylosin edisylate, tylosin esylate, tylosin formate, tylosin fumarate, tylosin gluceptate, tylosin gluconate, tylosin glucuronate, tylosin hexafluorophosphate, tylosin hibenzate, tylosin hydrochloride or chloride, tylosin hydrobromide or bromide, tylosin hydroiodide or iodide, tylosin isethionate, tylosin lactate, tylosin malate, tylosin maleate, tylosin malonate, tylosin mesylate, tylosin methylsulphate, tylosin naphthylate, tylosin 2-napsylate, tylosin nicotinate, tylosin nitrate, tylosin orotate, tylosin oxalate, tylosin palmitate, tylosin pamoate, tylosin phosphate, tylosin hydrogen phosphate, tylosin dihydrogen phosphate, tylosin pyroglutamate, tylosin saccharate, tylosin stearate, tylosin succinate, tylosin tannate, tylosin tartrate, tylosin tosylate, tylosin trifluoroacetate and tylosin xinofoate.

In certain aspects, the tylosin is present at a concentration from about 0.01% (w/v) to about 99.99% (w/v), about 0.01% (w/v) to about 99.99% (w/v), or about 0.01% (w/v) to about 5.0% (w/v).

In several embodiments, the compositions further include an ophthalmic demulcent. In some aspects, the demulcent is carboxymethylcellulose, hydroxyethylcellulose, hypromellose, methylcellulose, dextran, gelatin, glycerin, polyethylene glycol, polysorbate, propylene glycol, polyvinyl alcohol, or providone.

In several aspects of the aforementioned compositions, the carrier suitable for ophthalmic application is water, such as sterile water, or a solution, such as a solution including an isotonic agent. In certain aspects, the isotonic agent is sodium chloride. In further aspects, the sodium chloride is present at a concentration of about 0.01% (w/v) to about 25.0% (w/v) or about 0.05% (w/v) to about 5.0% (w/v). In other aspects, the isotonic agent is boric acid. In yet further aspects, the boric acid is present at a concentration of about 0.01% (w/v) to about 25.0% (w/v) or about 0.05% (w/v) to about 5.0% (w/v).

In further aspects of the compositions, the carrier suitable for ophthalmic application is a cream, gel, ointment, or a plurality of microspheres in which each microsphere has a core, which includes the tylosin or pharmaceutically acceptable salt thereof, and a bioadhesive coat.

In some aspects of the compositions, the tylosin or pharmaceutically acceptable salt thereof is present at a concentration from about 0.01 mg/ml to about 500 mg/ml, or about 0.1 mg/ml to about 50 mg/ml.

The compositions described above further include benzalkonium chloride in certain embodiments. In some aspects, the benzalkonium chloride is present at a concentration from about 0.01% (w/v) to about 99.99% (w/v), or about 0.01 mg/ml. In further aspects, the carrier is water or a solution including benzalkonium chloride present at a concentration from about 0.001 mg/ml to about 0.10 mg/ml.

Certain embodiments relate to devices for administering the compositions described above. In several embodiments, a device includes a reservoir includes a composition described above and an applicator adapted to transfer the composition from the reservoir to the eye, wherein the reservoir is coupled to the applicator. In some aspects, the reservoir is a tube and the applicator is a bulb. In further aspects, the device is a dropper.

In other aspects, a device for administering a substance to the eye includes a container having a tip to facilitate drop formation, wherein the container comprises tylosin or a pharmaceutically acceptable salt thereof. In some aspects, the tip has a blunt end, the tip is non-metallic, and/or the tip is not a needle. In further aspects, the angle of the tip apex is greater than 15 degrees.

Several embodiments provided herein relate to methods of reducing eye stain in a subject comprising administering a therapeutically effective amount of a composition including a pharmaceutically acceptable carrier comprising tylosin or a pharmaceutically acceptable salt thereof described above to the subject, wherein the administration of the composition reduces eye stain. In certain aspects of the aforementioned methods, the composition is administered to the subject opthalmically. In other aspects, such methods further include identifying a subject in need of eye stain reduction.

In various aspects, the subject is a domesticated animal, or more particularly a mammal, such as a dog or cat. In certain aspects of the methods of reducing eye stain in a dog, the dog is one of the following breeds: Maltese, Poodle, Shih-tzu, Pekingese, Pug, Cocker Spaniel, Bulldog, Bedlington Terrier, Bichon Frise, Brittany, Brussel Griffon, Chihuahua, Coton de Tulear, Havanese, Japanese Chin, King Charles Cavalier, Lhapsa Apso, Papillon, Pomeranian, Saint Bernard, Schnauzer, Sharpei, Silky Terrier, and Springer Spaniel. In other aspects of the methods of reducing eye stain in a cat, the cat is one of the following breeds: Devon Rex, Exotic Shorthair, Himalayan, Persian, Ragdoll, and Scottish Fold.

In several embodiments relating to methods of reducing eye stain in a subject, administration of the composition is effective to reduce bacterial or yeast infection of the eye, thereby reducing the eye stain. In certain aspects, the bacterial infection is a Ptyrosporin infection or a Red Yeast infection.

DETAILED DESCRIPTION

Embodiments provided herein relate to compositions, methods, and devices useful for treating stain in a subject. In a preferred embodiment, the subject is an animal and the stain is eye stain. As referred to herein, "eye stain" and "tear stain" are used interchangeably and refer to the stain on an animal's body, especially the hair, typically deposited in regions that come into contact with tears, saliva, or urine. In some embodiments, "eye stain" also includes any odor associated with the stain. Although the term "eye stain" includes staining around a subject's eyes, the term as used herein is more general and is also meant to include staining, especially of the hair, in areas of the body that come in contact with tears, saliva, or urine. Accordingly, "eye stain" can refer to the stain on an animal's skin or hair in the eye, mouth, leg, and genital areas. It will be understood that the term "hair" includes animal fur.

Generally, eye stain appears red or brown and is especially pronounced in light-colored animals. The eye stain treatable with the compositions and methods described herein is not limited to a particular etiology. Eye stain is thought to have a number of causes relating to excess tearing. Embodiments provided herein are contemplated as being useful for treating eye stain whether caused, for example, by chromodacryorrhea (the overproduction of tears with an excessive secretion of ferroporphyrins in tears, saliva and urine), bacterial or yeast infections, diet, and/or genetic factors. In several embodiments, compositions described herein can treat eye stain by killing or preventing growth of bacteria or yeast responsible for the eye stain.

Subjects

As used herein, a "subject" is generally any animal that may benefit from administration of the compositions described herein. In several embodiments, the compositions can be administered to a mammal. In various embodiments, the therapeutic agents can be administered to a veterinary animal subject, especially companion animals. In some embodiments, the therapeutic agents can be administered to a model experimental animal subject.

Figure 1:
FIG. 1 is a photograph of a canine with eye stain.

In several embodiments, the compositions provided herein can be administered to a domesticated animal, such as a dog or cat. Certain breeds of dogs are particularly prone to having eye stain and can be treated with the compositions provided herein (See e.g. FIG. 1). Examples of dog breeds that can be treated for eye stain include, but are not limited to, Akita, American Bulldog, American Eskimo Dog, Bedlington Terrier, Bichon Frise, Brittany, Brussels Griffon, Cairn Terrier, Chihuahua, Chinese Crested, Cocker Spaniel, Corgi, Coton de Tulear, Dachshund, Espanol Toy Spaniel, French Bulldog, Golden Retriever, Havanese, Japanese Chin, Cavalier King Charles Spaniel Lhasa Apso, Lion Dog, Maltese, Maltipoo, Miniature Schnauzer, Papillion, Pekingese, Pomeranian, Poodle, Pug, Saint Bernard, Sharpei, Schnauzer, Shih Tzu, Silky Terrier, Springer Spaniel, and West Highland White Terrier.

Figure 2:
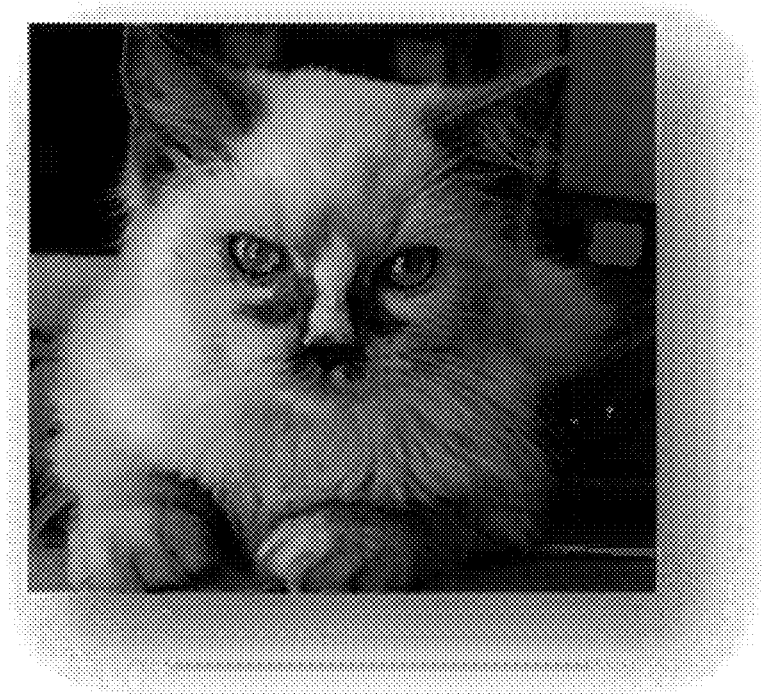
FIG. 2 is photograph of a feline with eye stain.

Certain breeds of cats are particularly prone to having eye stain and can be treated with the compositions provided herein (See e.g. FIG. 2). Examples of cat breeds that can be treated for eye stain include, but are not limited to, Abyssinians, Aegeans, Balinese, Birmans, Bobtails, Bombays, Burmese, Burmillas, Chartreaux, Cornish Rex, Cymrics, Devon Rex, Domestic Shorthairs, Exotic Shorthairs, Himalayans, Javanese, Korats, Manx, Minskins, Munchkins, Nebelungs, Persians, Ragamuffins, Ragdolls, Savannahs, Scottish Folds, Siamese, Snowshoes, Sokokes, Somalis Sphinx, Tonkinese and Toygers.

Compositions

Tylosin and Pharmaceutically Acceptable Salts Thereof

In several embodiments, compositions provided herein useful for treating eye stain comprise tylosin or a pharmaceutically acceptable salt thereof and a carrier suitable for ophthalmic application. Tylosin is a macrolide-class antibiotic used in veterinary medicine. It has a broad spectrum of activity against gram positive organisms, including *Staphylococci, Streptococci, Corynebacteria*, and *Erysipelothrix*, and has some activity against gram negative organisms. Tylosin's bacteriostatic effect is mediated through binding to the 50S subunit of the bacterial ribosome, thereby inhibiting protein synthesis.

It will be appreciated that other macrolides and compounds having structural similarities to macrolides can have an effect similar to Tylosin when administered directly to the eye. Other macrolides include, for example, azithromycin, erythromycin, clarithromycin, roxithromycin and josamycin.

By "pharmaceutically acceptable salts" is meant any of the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the therapeutic compounds described herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

Where appropriate, tylosin can be converted to its pharmaceutically acceptable salts prior to use in the preparation of a pharmaceutical composition contemplated by the invention. For example, pharmaceutically acceptable salts can be obtained by reacting tylosin with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting tylosin with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

Accordingly, in several embodiments compositions can comprise a pharmaceutically acceptable salt of tylosin including one or more of tylosin acetate, tylosin adipate, tylosin aspartate, tylosin benzoate, tylosin besylate, tylosin bicarbonate or carbonate, tylosin bisulphate or sulphate, tylosin borate, tylosin camsylate, tylosin citrate, tylosin cyclamate, tylosin edisylate, tylosin esylate, tylosin formate, tylosin fumarate, tylosin gluceptate, tylosin gluconate, tylosin glucuronate, tylosin hexafluorophosphate, tylosin hibenzate, tylosin hydrochloride or chloride, tylosin hydrobromide or bromide, tylosin hydroiodide or iodide, tylosin isethionate, tylosin lactate, tylosin malate, tylosin maleate, tylosin malonate, tylosin mesylate, tylosin methylsulphate, tylosin naphthylate, tylosin 2-napsylate, tylosin nicotinate, tylosin nitrate, tylosin orotate, tylosin oxalate, tylosin palmitate, tylosin pamoate, tylosin phosphate, tylosin hydrogen phosphate, tylosin dihydrogen phosphate, tylosin pyroglutamate, tylosin saccharate, tylosin stearate, tylosin succinate, tylosin tannate, tylosin tartrate, tylosin tosylate, tylosin trifluoroacetate, or tylosin xinofoate.

In some embodiments of the invention, pharmaceutical compositions comprising a concentration of tylosin or a pharmaceutically acceptable salt thereof from about 0.01% (w/v) to about 99.99% (w/v) are contemplated. In additional embodiments, pharmaceutical compositions comprising a concentration of tylosin or a pharmaceutically acceptable salt thereof from about 0.2% (w/v) to about 20% (w/v) are contemplated. In other embodiments, pharmaceutical compositions comprise less than about 0.1% (w/v) of tylosin or a pharmaceutically acceptable salt thereof. The pharmaceutical compositions according to still other embodiments of the invention comprise about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 35% (w/v), about 40% (w/v), about 45% (w/v), about 50% (w/v), about 55% (w/v), about 60% (w/v), about 65% (w/v), about 70% (w/v), about 75% (w/v), about 80% (w/v), about 85% (w/v), about 90% (w/v), about 95% (w/v), about 99% (w/v), or a concentration of tylosin or a pharmaceutically acceptable salt thereof in between any of the aforementioned concentrations.

Pharmaceutical Forms

The compositions described herein for treating eye stain can be administered in a variety of pharmaceutical forms. As such, pharmaceutical compositions comprising tylosin or a pharmaceutically acceptable salt thereof and a carrier suitable for ophthalmic application are provided. In several embodiments, the compositions comprising tylosin or a pharmaceutically acceptable salt thereof are administered opthalmically to the eye or around the eye.

"Carriers suitable for ophthalmic application" as used herein include pharmaceutically acceptable carriers, excipients, or stabilizers that are nontoxic to the eye at the concentrations employed. In several embodiments, the carrier suitable for ophthalmic application is an aqueous pH buffered solution. Examples of carriers suitable for ophthalmic application include, but are not limited to, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG).

Non-limiting examples of carriers suitable for ophthalmic application include, but are not limited to, water, isotonic solutions, buffered solutions, ointments, gels or other solvents. In several embodiments, the isotonic solution can include sodium chloride or boric acid at a concentration of about 0.01% (w/v) to about 25% (w/v), or more particularly about 0.05% (w/v) to about 5.0% (w/v).

In certain embodiments, the solvents are sterile. Thus, a sterile pharmaceutical composition can be prepared by mixing sterile ingredients aseptically. Alternatively, the sterile pharmaceutical composition can be prepared by first mixing the ingredients then sterilizing the final preparation.

The compositions described herein may be in the pharmaceutical form of liquid, gel, ointment, or cream preparations. Liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, e.g., sorbitol, syrup, methyl cellulose, glucose syrup, gelatin, emulsifying agents, e.g., lecithin, sorbitan monooleate, or acacia; oils, oily esters such as glycerine, propylene glycol, or ethyl alcohol; preservatives such as methyl or propyl p-hydroxybenzoate or sorbic acid.

Liquid dosage forms include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying agents, and suspending agents.

Pharmaceutical compositions that are particularly useful for administration-directly to the eye include aqueous solutions and/or suspensions formulated as eye drops and thickened solutions and/or suspensions formulated as ophthalmic gels or ointments. Aqueous solutions and diluents for suspensions that are used in preparation of eye drops can include distilled water, physiological saline, and the like. Non-aqueous solutions and diluents for suspensions can include vegetable oil, liquid paraffin, mineral oil, propylene glycol, p-octyldodecanol as well as similar solvents.

Various additives may be contained in eye drops, ophthalmic gels and/or ophthalmic ointments as needed. These include, but not limited to, buffering agents, isotonizers, preservatives, thickeners, stabilizers, antizoxidants, pH-adjusting agents, chelating agents. Buffering agents are added to keep the pH constant and can include pharmaceutically acceptable buffering agents such as borate buffer, citrate buffer, tartrate buffer, phosphate buffer, and acetate buffer. Buffering agents are included in an amount that provides sufficient buffer capacity for the expected physiological conditions.

In addition to a buffer, isotonizers can be added to eye drops to make the preparation isotonic with the tear. Isotinizers include, but are not limited to, sugars such as glucose, sucrose and fructose; sugar alcohols such as mannitol and sorbitol; polyhydric alcohols such as glycerol, polyethylene glycol and propylene glycol; and salts such as sodium chloride, sodium citrate, boric acid, and sodium succinate. Isotonizers are added in an amount that makes the osmotic pressure of the eye drop equal to that of the tear.

Preservatives can be added to maintain the integrity of the eye drop and/or ophthalmic ointment. Examples of preservatives include, but are not limited to, benzalkonium chloride, parabens, chlorobutanol and benzylic alcohol. In several embodiments, the concentration of preservative (e.g. benzalkonium chloride) in the composition can range from about 0.001 mg/ml to about 0.1 mg/ml. In some embodiments, the concentration of preservative (e.g. benzalkonium chloride) is about 0.01 mg/ml.

In some embodiments, thickeners are used to increase the viscosity of ophthalmic preparations such as eye drops, ophthalmic gels and/or ophthalmic ointments. Thickeners that can be used include, but are not limited to, glycerol, polyethylene glycol and carboxyvinyl polymers.

In addition to the above, in some embodiments, it is desirable to use additional agents which include, but are not limited to, stabilizers such as sodium sulfite and propylene glycol; antioxidants such as ascorbic acid, sodium ascorbate, butylated hydroxy toluene (BHT), butylated hydroxyanisole (BHA), tocopherol, sodium thiosulfate; and/or chelating agents such as ethylene-diamine-tetra-acetic acid (EDTA), ethylene glycol-bis-(2-aminoethyl)-N,N,N',N'-tetraacetic acid (EGTA) and sodium citrate. In several embodiments, the concentration of stabilizer (e.g. EDTA) in the composition can range from about 0.01 mg/ml to about 1.0 mg/ml. In some embodiments, the concentration of stabilizer (e.g. EDTA) in the composition is about 0.2 mg/ml.

Eye drops, ophthalmic gels and/or ophthalmic ointments can be prepared by aseptic manipulation or alternatively sterilization is performed at a suitable stage of preparation. Sterilization methods can include, but are not limited to, heat sterilization, irradiation and filtration.

Ophthalmic ointments (eye ointments) can be aseptically prepared by mixing the active ingredient into a base that is used for preparation of eye ointments followed by formulation into pharmaceutical preparations with any method known in the art. Typical bases for eye ointments are exemplified by vaseline, jelene 50, plastibase and macrogol. In addition, surfactants may be added to increase hydrophilia.

Microphere Carriers

In several embodiments, the carrier suitable for ophthalmic application is a microsphere, which comprises tylosin or a pharmaceutically acceptable salt thereof. As used herein, the term "microsphere" refers to a drug delivery vehicle not limited to any size, shape, or dimension. As such, in some embodiments, "microsphere" as used herein is a broad term that generally encompasses particles commonly referred to as nanospheres, nanoparticles, microcapsules, nanocapsules, microspheres, microparticles, colloids, aggregates, flocculates, insoluble salts, emulsions and insoluble complexes, any of which can comprise inorganic materials, polymers, polypeptides, proteins, lipids, and surfactants. In preferred embodiments, a microsphere comprises nanospheres and/or nanocapsules. In other preferred embodiments, a microsphere comprises microcapsules.

Microspheres are not necessarily spherical, but generally have an average diameter, regardless of their shape, of about less than or equal to about 20 microns, since particles of these dimensions are not believed to irritate the eye. However, it will be appreciated that microspheres 20 microns and larger can be applied to the eye. Microspheres larger than 20 microns can be beneficial for use in species or individual subjects having eyes with decreased sensity to physical irritation. Spheres having an average diameter, regardless of their shape, of less than about 1 micron (i.e. in the nanometer range) are often referred to as "nanospheres." As referred to herein, the term "microspheres" is meant to include spheres in both the micron and nanometer size range, such that the term "microspheres" is meant to encompass the common meaning of "nanospheres." In some embodiments, the microsphere is a solid or a semi-solid. In some embodiments, the microsphere is generally centrosymmetric. In some embodiments, the microsphere contains a generally uniform dispersion of solid components.

Accordingly, in several embodiments microspheres can have a characteristic dimension of about 50 µm, 40 µm, 30 µm, 20 µm, 15 µm, 10 µm, 5 µm, 4 µm, 3 µm, 2 µm, or 1 µm, or any size in between any of the aforementioned dimensions. In several embodiments, microspheres can have a characteristic dimension less than about 1 micrometer, where the characteristic dimension of a particle is the diameter of a perfect sphere having the same volume as the particle. For example, the microsphere may have a characteristic dimension that is less than 1000 nm, 900 nm, 800 nm, 700 nm, 600 nm, 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm, or 20 nm, or any number in between the aforementioned sizes. In some embodiments, the microsphere can have a characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm, or any number in between the aforementioned sizes. In other embodiments, the microsphere can have a characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm. Tylosin or a pharmaceutically acceptable salt thereof can be incubated with the microspheres, and thereby be associated, embedded, encapsulated, loaded, and/or integrated with microsphere.

In some embodiments, a composition comprises a population or plurality of microspheres, and the population or plurality of microspheres can have an average characteristic dimension as described above. A population or plurality of microspheres can include at least 20 particles, at least 50 particles, at least 100 particles, at least 300 particles, at least 1,000 particles, at least 3,000 particles, at least 10,000 particles, or greater than 10,000 particles. Various embodiments of the present invention are directed to such populations of particles. For instance, in some embodiments, the particles can each be substantially the same shape and/or size ("monodisperse"). For example, the particles can have a distribution of characteristic dimensions such that no more than about 5 or 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater than the average characteristic dimension of the particles. In some embodiments, no more than about 5% of the particles have a characteristic dimension greater than about 5%, about 3%, about 1%, about 0.3%, about 0.1%, about 0.03%, or about 0.01% greater than the average characteristic dimension of the particles.

In some embodiments, microspheres comprise a material that is biologically inert and can be physiologically tolerated without significant adverse effects by biological systems. Further, a microsphere can be comprised of a biodegradable material. It will be understood that there are no restrictions on the physical parameters of a microsphere in embodiments provided herein. The physical parameters of a microsphere can be optimized, with the desired effect governing the choice of size and shape.

The microsphere can comprise a variety of materials including, but not limited to, polymers such as polystyrene, silicone rubber, polycarbonate, polyurethanes, polypropylenes, polymethylmethacrylate, polyvinyl chloride, polyesters, polyethers, and polyethylene.

Additional examples of useful polymers include, but are not limited to, the following: polyethylene glycol (PEG); poly(lactic acid-co-glycolic acid) (PLGA); copolymers of PLGA and PEG; copolymers of poly(lactide-co-glycolide) and PEG; polyglycolic acid (PGA); copolymers of PGA and PEG; poly-L-lactic acid (PLLA); copolymers of PLLA and PEG; poly-D-lactic acid (PDLA); copolymers of PDLA and PEG; poly-D,L-lactic acid (PDLLA); copolymers of PDLLA and PEG; poly(ortho ester); copolymers of poly(ortho ester) and PEG; poly(caprolactone); copolymers of poly(caprolactone) and PEG; polylysine; copolymers of polylysine and PEG; polyethylene imine; copolymers of polyethylene imine and PEG; polyhydroxyacids; polyanhydrides; polyhydroxyalkanoates, poly(L-lactide-co-L-lysine); poly(serine ester); poly(4-hydroxy-L-proline ester); poly-α-(4-aminobutyl)-L-glycolic acid; derivatives thereof; combinations thereof; and copolymers thereof.

Additional examples of polymeric and non-polymeric materials that can be used is several embodiments include, but are not limited to, poly(lactide), poly(hydroxybutyrate), poly (beta-amino) esters and/or copolymers thereof. Alternatively, the particles can comprise other materials, including but not limited to, poly(dienes) such as poly(butadiene) and the like; poly(alkenes) such as polyethylene, polypropylene and the like; poly(acrylics) such as poly(acrylic acid) and the like; poly(methacrylics) such as poly(methyl methacrylate), poly (hydroxyethyl methacrylate), and the like; poly(vinyl ethers); poly(vinyl alcohols); poly(vinyl ketones); poly(vinyl halides) such as poly(vinyl chloride) and the like; poly(vinyl nitriles), poly(vinyl esters) such as poly(vinyl acetate) and the like; poly(vinyl pyridines) such as poly(2-vinyl pyridine), poly(5-methyl-2-vinyl pyridine) and the like; poly(styrenes); poly (carbonates); poly(esters); poly(orthoesters); poly(esteramides); poly(anhydrides); poly(urethanes); poly(amides); cellulose ethers such as methyl cellulose, hydroxyethyl cellulose, hydroxypropyl methyl cellulose and the like; cellulose esters such as cellulose acetate, cellulose acetate phthalate, cellulose acetate butyrate, and the like; poly(saccharides), protein, polypeptides, gelatin, starch, gums, resins and the like. These materials may be used alone, as physical mixtures (blends), or as copolymers.

Biodegradable, biopolymer (e.g. polypeptides such as BSA, polysaccharides, etc.), other biological materials (e.g. carbohydrates), and/or polymeric compounds are also suitable for use as a microsphere scaffold. In various embodiments, the microsphere is negatively charged. The microspheres may themselves have a negative charge or alternatively a positive charge on them or may be modified to attach a negative charge or positive charge to the scaffold, such as, but not limited to, aldehyde, amine, carboxyl, sulfate, or hydroxyl groups. Factors such as microsphere surface charge and hydrophilic/hydrophobic balance of these polymeric materials can be achieved by synthetic modification of the polymers. Such synthetic modification is known in the art and contemplated herein. Various methods for producing the negatively charged microspheres are described in U.S. Pat. No. 7,390,384, which is incorporated herein by reference in its entirety.

Liposome Carriers

In several embodiments, the carrier suitable for ophthalmic application is a liposome, which comprises tylosin or a pharmaceutically acceptable salt thereof. In various embodiments, tylosin or a pharmaceutically acceptable salt thereof is encapsulated inside the liposome. As used herein, the term "liposome" refers to a vesicle composed of amphiphilic lipids arranged in a relatively spherical bilayer or bilayers.

Liposomes are unilamellar or multilamellar vesicles which have a membrane formed from a lipophilic material and an aqueous interior. The aqueous interior portion contains the composition to be delivered. Phospholipids used for liposome formation include, but are not limited to, natural phospholipids such as egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanolamine, diphosphatidyl glycerol. Liposome preparation is described, for example, in U.S. Pat. Nos. 7,208,174, 7,108,863, 5,192,549, 6,958,241, and in Ann. Rev. Biophys. Bioeng., 9, 467 (1980), "Liposomes" (Ed. by M. J. Ostro, Marcel Dekker, Inc.) the entire contents of which are incorporated herein by reference. In several embodiments, tylosin or a pharmaceutically acceptable salt thereof is contained in multilamellar liposomes.

When phospholipids and many other amphipathic lipids are dispersed gently in an aqueous medium they swell, hydrate and spontaneously form multilamellar concentric bilayer vesicles with layers of aqueous media separating the lipid bilayers. These systems commonly are referred to as multilamellar liposomes or multilamellar vesicles (MLV) and usually have diameters of from 0.2 µm to 5 µm. Sonication of MLV results in the formation of small unilamellar vesicles (SUV) with diameters usually in the range of 20 to 100 nm, containing an aqueous solution in the core. Multivesicular liposomes (MVL) differ from multilamellar liposomes in the random, non-concentric arrangement of chambers within the liposome. Amphipathic lipids can form a variety of structures other than liposomes when dispersed in water, depending on the molar ratio of lipid to water, but at low ratios the liposome is the preferred structure.

The physical characteristics of liposomes generally depend on pH and ionic strength. They characteristically show low permeability to ionic and polar substances, but at certain temperatures can undergo a gel-liquid crystalline phase (or main phase) transition dependent upon the physical properties of the lipids used in their manufacture which markedly alters their permeability. The phase transition involves a change from a closely packed, ordered structure, known as the gel state, to a loosely packed, less-ordered structure, known as the liquid crystalline state.

Various types of lipids differing in chain length, saturation, and head group have been used in liposomal formulations for years, including the unilamellar, multilamellar, and multivesicular liposomes mentioned above.

There are at least three types of liposomes. The teen "multivesicular liposomes (MVL)" generally refers to man-made, microscopic lipid vesicles comprising lipid membranes enclosing multiple non-concentric aqueous chambers. In contrast, "multilamellar liposomes or vesicles (MLV)" have multiple "onion-skin" concentric membranes, in between which are shell-like concentric aqueous compartments. Multilamellar liposomes and multivesicular liposomes characteristically have mean diameters in the micrometer range, usually from 0.5 to 25 μm. The term "unilamellar liposomes or vesicles (ULV)" generally refers to liposomal structures having a single aqueous chamber, usually with a mean diameter range from about 20 to 500 nm.

Multilamellar and unilamellar liposomes can be made by several relatively simple methods. A number of techniques for producing ULV and MLV are described in the art (for example in U.S. Pat. No. 4,522,803 to Lenk; U.S. Pat. No. 4,310,506 to Baldeschweiler; U.S. Pat. No. 4,235,871 to Papahadjopoulos; U.S. Pat. No. 4,224,179 to Schneider, U.S. Pat. No. 4,078,052 to Papahadjopoulos; U.S. Pat. No. 4,394,372 to Taylor U.S. Pat. No. 4,308,166 to Marchetti; U.S. Pat. No. 4,485,054 to Mezei; and U.S. Pat. No. 4,508,703 to Redziniak).

By contrast, production of multivesicular liposomes generally requires several process steps. Briefly, a common method for making MVL is as follows: The first step is making a "water-in-oil" emulsion by dissolving at least one amphipathic lipid and at least one neutral lipid in one or more volatile organic solvents for the lipid component, adding to the lipid component an immiscible first aqueous component and a biologically active substance to be encapsulated, and optionally adding, to either or both the lipid component and the first aqueous component, an acid or other excipient for modulating the release rate of the encapsulated biologically active substances from the MVL. The mixture is emulsified, and then mixed with a second-immiscible aqueous component to form a second emulsion. The second emulsion is mixed either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them (see Kim et al., Biochem. Biophys. Acta, 728:339-348, 1983). For a comprehensive review of various methods of ULV and MLV preparation, refer to Szoka, et al. Ann. Rev. Biophys. Bioeng. 9:465-508, 1980.

Making multivesicular liposomes can involve inclusion of at least one amphipathic lipid and one neutral lipid in the lipid component. The amphipathic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phosphatidylglycerols, phosphatidylserines, phosphatidylinositols, phosphatidic acids, etc. Examples of cationic amphipathic lipids are diacyl trimethylammonium-propane and ethyl phosphatidylcholine. Examples of neutral lipids include diglycerides, such as diolein, dipalmitolein, and mixed caprylin-caprin diglycerides; triglycerides, such as triolein, tripalmitolein, trilinolein, tricaprylin, and trilaurin; vegetable oils, such as soybean oil; animal fats, such as lard and beef fat; squalene; tocopherol; and combinations thereof. Additionally, cholesterol or plant sterols can be used in making multivesicular liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

In several embodiments described herein, liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In various embodiments, liposomes can be composed of phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions can be formed from dimyristoyl phosphatidylglycerol, while anionic fusogenic liposomes can be formed from dioleoyl phosphatidylethanolamine (DOPE). Another type of liposomal composition can be formed from phosphatidylcholine (PC) such as, for example, soybean PC, and egg PC. Another type can be formed from mixtures of phospholipid and/or phosphatidylcholine and/or cholesterol.

Examples of phospholipids suitable for use in several embodiments include but are not limited to DOPC or DC18: 1PC=1,2-dioleoyl-sn-glycero-3-phosphocholine; DLPC or DC12:0PC=1,2-dilauroyl-sn-glycero-3-phosphocholine; DMPC or DC14:0PC=1,2-dimyristoyl-sn-glycero-3-phosphocholine; DPPC or DC16:0PC=1,2-dipalmitoyl-sn-glycero-3-phosphocholine; DSPC or DC18:0PC=1,2-distearoyl-sn-glycero-3-phosphocholine; DAPC or DC20:0PC=1,2-diarachidoyl-sn-glycero-3-phosphocholine; DBPC or DC22: 0PC=1,2-dibehenoyl-sn-glycero-3-phosphocholine; DC16: 1PC=1,2-dipalmitoleoyl-sn-glycero-3-phosphocholine; DC20:1PC=1,2-dieicosenoyl-sn-glycero-3-phosphocholine DC22:1PC=1,2-dierucoyl-sn-glycero-3-phosphocholine; DPPG=1,2-dipalmitoyl-sn-glycero-3-phosphoglycerol; DOPG=1,2-dioleoyl-sn-glycero-3-phosphoglycerol.

Additional examples of phospholipids suitable for use in several embodiments provided herein include but are not limited to those listed in Table 1 below.

TABLE 1

| Abbreviation | CAS | Name | Type |
|---|---|---|---|
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . . )] (Sodium Salt) | Phosphatidylglycerol |
| DLOPC | 998-06-1 | 1,2-Dilinoleoyl-sn-glycero-3-phosphocholine | Phosphatidylcholine |
| DLPA-NA | | 1,2-Dilauroyl-sn-glycero-3-phosphate (Sodium Salt) | Phosphatidic acid |
| DLPC | 18194-25-7 | 1,2-Dilauroyl-sn-glycero-3-phosphocholine | Phosphatidylcholine |
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . . )] (Sodium Salt) | Phosphatidylglycerol |
| DLPG-NH4 | | 1,2-Dilauroyl-sn-glycero-3[Phospho-rac-(1-glycerol . . . )] (Ammonium Salt) | Phosphatidylglycerol |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . . )] (Sodium Salt) | Phosphatidylglycerol |
| DMPG-NH4 | | 1,2-Dimyristoyl-sn-glycero-3[Phospho-rac-(1-glycerol . . . )] (Ammonium Salt) | Phosphatidylglycerol |
| DMPG-NH4/NA | | 1,2-Dimyristoyl-sn-glycero-3[Phospho-rac-(1-glycerol . . . )] (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |
| DOPG-NA | 62700-69-0 | 1,2-Dioleoyl-sn-glycero-3[Phospho-rac-(1-glycerol . . . )] (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol . . . )] (Sodium Salt) | Phosphatidylglycerol |
| DPPG-NH4 | 73548-70-6 | 1,2-Dipalmitoyl-sn-glycero-3[Phospho-rac-(1-glycerol . . . )] (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . . )] (Sodium Salt) | Phosphatidylglycerol |

TABLE 1-continued

| Abbreviation | CAS | Name | Type |
|---|---|---|---|
| DSPG-NH4 | 108347-80-4 | 1,2-Distearoyl-sn-glycero-3[Phospho-rac-(1-glycerol . . . ) (Ammonium Salt) | Phosphatidylglycerol |
| DSPS-NA | | 1,2-Distearoyl-sn-glycero-3-phosphoserine (Sodium Salt) | Phosphatidylserine |
| Egg Sphingomyelin | | | |
| empty Liposome | | | |
| EPC | | Egg-PC | Phosphatidylcholine |
| HEPC | | Hydrogenated Egg PC | Phosphatidylcholine |
| HSPC | | High purity Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |
| Milk Sphingomyelin | | | |
| MPPC | | 1-Myristoyl-2-palmitoyl-sn-glycero 3-phosphocholine | Phosphatidylcholine |
| MSPC | | 1-Myristoyl-2-stearoyl-sn-glycero-3-phosphocholine | Phosphatidylcholine |
| PMPC | | 1-Palmitoyl-2-myristoyl-sn-glycero-3-phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol) . . . ] (Sodium Salt) | Phosphatidylglycerol |
| PSPC | | 1-Palmitoyl-2-stearoyl-sn-glycero-3-phosphocholine | Phosphatidylcholine |
| SMPC | | 1-Stearoyl-2-myristoyl-sn-glycero-3-phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholine |

Furthermore, liposomes of the present embodiments can be of various sizes. For example, the diameter of a liposome in various embodiments can be about 300 nm, about 295 nm, about 290 nm, about 285 nm, about 280 nm, about 275 nm, about 270 nm, about 265 nm, about 260 nm, about 255 nm, about 250 nm, about 245 nm, about 240 nm, about 235 nm, about 230 nm, about 225 nm, about 220 nm, about 215 nm, about 210 nm, about 205 nm, about 200 nm, about 195 nm, about 190 nm, about 185 nm, about 180 nm, about 175 nm, about 170 nm, about 165 nm, about 160 nm, about 155 nm, about 150 nm, about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, or about 5 nm. In some embodiments, tylosin or a pharmaceutically acceptable salt thereof can be contained in liposomes that have a diameter of about 200 nm.

Various embodiments include pH sensitive liposomes. Without being bound by theory, it is believed that liposomes which are stable at neutral pH but release their contents at acidic pH can be used to deliver contents into the lysozymes of the cytoplasm, whereupon the contents are released.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized.

Examples of these charged molecules include but are not limited to oleic acid and cholesteryl hemisuccinate, which are negatively charged at neutral pH but become neutralized at pH 5. The effect of combining these together in a lipid bilayer is that at pH 9 all molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

By way of example and not limitation, pH sensitive liposomes can be produced by combining phosphatidylethanolamine and cholesteryl hemisuccinate (CHEMS) which destabilizes the liposome at a pH of about less than 4.5. Additionally, inclusion of oleic acid with phosphatidylethanolamine also destabilizes the lipid bilayer at a pH of about less than 6.5, and imparts a net negative charge to the liposome at neutral pH. Liposomes composed of a mixture of phosphatidylcholine and phosphatidylethanolamine are more pH sensitive than those composed of phosphatidylethanolamine alone. In several embodiments, liposomes comprise phospholipids, oleic acid, and cholesterol.

The liposomes of several embodiments described herein can be prepared by combining a phospholipid component with an aqueous component containing tylosin or a pharmaceutically acceptable salt thereof, whether present as a component of an extract or in isolated or purified form, under conditions which will result in vesicle formation. The phospholipid concentration should be adequate to form lamellar structures and the aqueous component should be compatible with stability of tylosin or a pharmaceutically acceptable salt thereof.

Phospholipids and aqueous components can be combined to form vesicles, for example, by drying the phospholipids onto glass and then dispersing them in the aqueous component; injecting phospholipids dissolved in a vaporizing or non-vaporizing organic solvent into the aqueous component which has previously been heated; and dissolving phospholipids in the aqueous phase with detergents and then removing the detergent by dialysis. Methods of producing liposomes in a microfluidizer and adjusting the shear pressure as a means to adjust liposome size are well known in the art.

Emulsions

In several embodiments, the carrier suitable for ophthalmic application is an emulsion, which comprises tylosin or a pharmaceutically acceptable salt thereof. Emulsions are typically heterogeneous systems of one liquid dispersed in another in the form of droplets usually exceeding 0.1 µm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment of the invention, a pharmaceutical composition comprising tylosin or a pharmaceutically acceptable salt thereof is formulated as a microemulsion. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously. Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions can form spontaneously when their components are brought together at ambient temperature. Microemulsions have also been effective in the transdermal delivery of active components in both cosmetic and pharmaceutical applications.

In some embodiments of the invention, microemulsions can also contain additional components and additives such as sorbitan monostearate (Grill 3), Labrasol, and penetration enhancers to improve the properties of the formulation and to enhance the absorption of the therapeutic compounds described herein. Penetration enhancers used in the microemulsions can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92).

Surfactants

Any of the embodiments drawn to compositions including microspheres or liposomes, or emulsions can further include one or more surfactants known in the art.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the 'head') provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. Popular members of the anionic surfactant class are the alkyl sulfates and the soaps. Also contemplated as examples of anionic surfactants that can be used in several embodiments include stearic acid and sodium behenoyl actylate.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in "Pharmaceutical Dosage Forms," Marcel Dekker, Inc., New York, N.Y., 1988, p. 285). Preferably such surfactants are nonionic and may be in the form of silicones or organic nonionic surfactants.

Suitable silicone surfactants include but are not limited to polyorganosiloxane polymers that have amphiphilic properties, for example contain hydrophilic radicals and lipophilic radicals. These silicone surfactants may be liquids or solids at room temperature. Examples of silicone surfactants that can be used in various embodiments include, but are not limited to: dimethicone copolyols, alkyl dimethicone copolyols, and emulsifying silicone elastomers. Emulsifying silicone elastomers are elastomers that have one or more hydrophilic groups such as hydroxyl, oxyethylene, and the like bonded thereto so as to confer hydrophilic properties to the elastomer. Suitable organic nonionic surfactants may include alkoxylated alcohols or ethers formed by the reaction of an alcohol with a polyalkyleneoxide containing repeating units of alkylene oxide. Preferably, the alcohol is a fatty alcohol having 6 to 30 carbon atoms. Examples of organic nonionic surfactants that can be used in various embodiments include, but are not limited to: steareth 2-100, beheneth 5-30, ceteareth 2-100, ceteareth-25, ceteth 1-45, and the like, which are formed by polyethyleneoxide with the corresponding stearyl/behenyl/cetyl alcohol (wherein the number as used herein designates the number of repeating units of ethylene oxide in the polyethyleneoxide). Other alkoxylated alcohols include esters formed by reaction of polymeric alkylene glycols with glyceryl fatty acid, such as PEG glyceryl oleates, PEG glyceryl stearate; or PEG polyhydroxyalkanotes such as PEG dipolyhydroxystearate wherein the number of repeating ethylene glycol units ranges from 3 to 1000. Nonionic surfactants formed by the reaction of a carboxylic acid with an alkylene oxide or with a polymeric ether are also suitable examples. Monomeric, homopolymeric, or block copolymeric ethers, alkoxylated sorbitan, alkoxylated sorbitan derivatives can also be used as nonionic surfactants in various embodiments.

Opthalmic Demulcents

In several embodiments, compositions comprising tylosin or a pharmaceutically acceptable salt thereof and a carrier suitable for ophthalmic application can further comprise an opthalmic demulcent. In some embodiments, an ophthalmic demulcent is an agent that provides a soothing sensation to the eye. In some embodiments, an ophthalmic demulcent protects and/or lubricates mucous membrane surfaces, thereby relieving dryness and irritation when applied to the eye. Any known demulcent suitable for opthalmic administration can be used in various embodiments related to a composition comprising tylosin or a pharmaceutically acceptable salt thereof and an opthalmic demulcent.

Examples of suitable ophthalmic demulcents that can be used in several embodiments include, but are not limited to, hydroxyethylcellulose, hydroxproplycellulose, hydroxypropyl methylcellulose, methylcellulose, polyvinyl alcohol, polyvinyl alcohol, cellulose ester, providone, hydroxypropyl guar, carboxymethylcellulose sodium, Dextran 70, dextrose, gelatin, glycerin, polyethylene glycol (e.g. PEG 300, PEG 400), polysorbates (e.g. Polysorbate 80), and propylene glycol. Additional demulcents known in the art that can be used in embodiments provided herein include, but are not limited to those described in U.S. Pat. Nos. 5,591,426, 5,106,615, 4,029,817, 3,767,788; 3,767,789; 3,856,919; 3,907,985; 3,920,810; 3,947,573; 3,987,163, 3,549,747, 4,131,651, 4,120,949, and 4,409,205, each of which is incorporated by reference herein in its entirety and for all purposes.

In some embodiments, carboxymethylcellulose can be added as an ophthalmic demulcent to a preparation of tylosin or a pharmaceutically acceptable salt thereof. Carboxymethylcellulose is a polymer that is obtainable in a variety of viscosities depending on the average polymer molecular weight. The use of both low viscosity and high viscosity carboxymethylcellulose is compatible with the pharmaceutical preparations described herein. It will be appreciated that increasing the viscosity grade of carboxymethylcellulose and/or the amount of this polymer present in the preparation will increase the viscosity of the preparation. In some embodiments, the viscosity of the preparation is sufficient to form a gel.

The concentration of a demulcent in pharmaceutical compositions contemplated in certain embodiments of the invention is generally less than that of tylosin or a pharmaceutically acceptable salt thereof. It will be appreciated, however, that pharmaceutical compositions which comprise concentrations of demulcent greater than the concentration of tylosin or a pharmaceutically acceptable salt thereof can be envisioned and are well within the scope of the invention.

For example, pharmaceutical compositions comprising a concentration of a demulcent from about 0.01% (w/v) to about 10% (w/v) can be prepared. According to some embodiments of the invention, pharmaceutical compositions comprise about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v) or more than 10% (w/v) of a demulcent.

Methods of Treating Eye Stain

Several embodiments provided herein relate to treating eye stain by administering to a subject a composition comprising tylosin or a pharmaceutically acceptable salt thereof and a carrier suitable for ophthalmic application described above. As used herein, to "treat" eye stain by administration of a composition comprising tylosin or a pharmaceutically acceptable salt thereof means that the visible stain on the subject's hair and/or associated odor is reduced or removed following administration of the composition as compared to the appearance and/or odor of the stain without administration of the composition. Treatment of eye stain includes reduction or removal of the stain and/or odor on the hair from any area on the subject in contact with tears, saliva, or urine. Such areas that can be treated with the compositions provided herein include the hair around the eyes, mouth, legs, buttocks, and genitals. Furthermore, "treating eye stain" can also include, in some embodiments, reduction of tear production or bad breath in a subject administered compositions comprising tylosin or a pharmaceutically acceptable salt thereof and a carrier suitable for ophthalmic application described herein.

Several embodiments provided herein relate to treating eye stain by administering to a subject a "therapeutically effective amount" of a composition comprising tylosin or a pharmaceutically acceptable salt thereof and a carrier suitable for ophthalmic application described above. As used herein, a "therapeutically effective amount" or "effective amount" is the amount of the compositions comprising tylosin or a pharmaceutically acceptable salt thereof and a carrier suitable for ophthalmic application that (1) reduces or removes eye stain, (2) reduces or removes an odor associated with the eye stain, (3) reduces tear production, and/or (4) reduces bad breath in the subject when administered a composition of the present embodiments.

Figure 3:
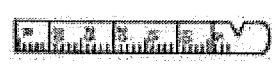
FIG. 3 is a diagram depicting the Schirmer Tear Test.
Figure 3:
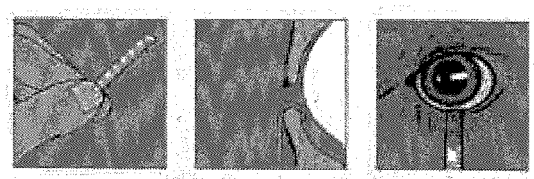
Figure 3:
Figure 3:
Figure 3:

Accordingly, a "therapeutically effective amount" or "effective amount" of a composition comprising tylosin or a pharmaceutically acceptable salt thereof includes the amount that reduces or removes the visible stain on the affected subject's hair or skin and/or reduces or removes an odor associated with the visible stain on the affected subject's hair or skin from any area on the subject that can come into contact with tears, saliva, or urine (e.g. hair around the eyes, mouth, legs, buttocks, and genitals). Alternatively or additionally, a "therapeutically effective amount" or "effective amount" of a composition comprising tylosin or a pharmaceutically acceptable salt thereof includes the amount that reduces tear production in the subject. Tests for measuring reduction of tear production are available in the art, such as the Schirmer Tear Test. As depicted in FIG. 3, the Schirmer Tear Test involves placing a paper test strip inside the lower eyelid of a subject and measuring the length of the moisture transferred from the eye onto the test strip.

The effective amount may depend on the age, weight, and other health conditions of the subject as well as the subject's hair color and extent of eye stain. Thus, the effective amount may not be the same in every subject to which the compositions provided herein are administered.

The effective amount of the compositions provided herein that are sufficient to treat eye stain in a subject can be administered in fixed doses with respect to the amount of tylosin or a pharmaceutically acceptable salt thereof. Such fixed doses can be, for example, about 1 µg, 50 µg, 75 µg, 100 µg, 150 µg, 200 µg, 250 µg, 300 µg, 350 µg, 400 µg, 500 µg, 550 µg, 600 µg, 700 µg, 800 µg, 900 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 60 mg, 65 mg, 70 mg, 75 mg, 80 mg, 85 mg, 90 mg, 100 mg, 150 mg, 200 mg, 250 mg, 300 mg, 350 mg, 400 mg, 450 mg, 500 mg, 600 mg, 700 mg, 800 mg, 900 mg, 1000 mg, 1250 mg, 1500 mg, 1750 mg, 2000 mg, 2250 mg, 2500 mg, 2750 mg, 3000 mg, 3500 mg, 4000 mg, 4500 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500 mg, 10,000 mg, or any number in between any two of the aforementioned doses at a frequency according to a treatment course that can last from several days to several months, or until a eye stain is reduced or removed to a desired extent. In some embodiments, the doses are not fixed but are administered at variable levels or on a variable schedule. For example, in some embodiments, the doses may increase over time, whereas in other embodiments, the doses may decrease over time.

Optimal dosing schedules can be calculated from measurements of drug accumulation in the body of the patient. Persons of ordinary skill can easily determine optimum dosages, dosing methodologies and repetition rates. Optimum dosages may vary depending on the subject.

The pharmaceutical compositions described herein can be administered as a single dose or in multiple doses; administered either as individual therapeutic agents or in combination with other therapeutic agents; and combined with conventional therapies, which may be administered sequentially or simultaneously. In several embodiments, daily dosages of the present compositions are administered opthalmically at about 1 drop per eye, about 2 drops per eye, about 3 drops per eye, about 4 drops per eye, about 5 drops per eye, about 6 drops per eye, about 7 drops per eye, about 8 drops per eye, about 9 drops per eye, about 10 drops per eye, about 11 drops per eye, about 12 drops per eye or more than about 12 drops per eye, each drop having an approximate volume of less than 25 µl, about 25 µl, about 50 µl, about 100 µl, about 125 µl, about 150 µl, about 175 µl, about 200 µl, about 225 µl, about 250 µl, about 275 µl, about 300 µl, about 325 µl, about 350 µl, about 375 µl, about 400 µl, about 425 µl, about 450 µl, about 475 µl, about 500 µl, about 525 µl, about 550 µl, about 575 µl, about 600 µl, about 625 µl, about 650 µl, about 675 µl, about 700 µl, about 725 µl, about 750 µl, about 775 µl, about 800 µl, about 825 µl, about 850 µl, about 875 µl, about 900 µl, about 925 µl, about 950 µl, about 975 µl, about 1000 µl, greater than 1000 µl, or any volume in between any of the aforementioned volumes.

In another embodiment of the invention, daily administration schedule for the present ophthalmic formulations is about 1 time per day, about 2 times per day, about 3 times per day, about 4 times per day, about 5 times per day, about 6 times per day, about 7 times per day, about 8 times per day, about 9 times per day, about 10 times per day, about 11 times per day, about 12 times per day or more than about 12 times per day. Dosages can be standardized for instance by means of a standard pharmacopeial medicinal dropper of 3 mm in external diameter, which when held vertically delivers 20 drops of water of total weight of 0.9 to 1.1 grams at 25° C.

When administered according to the dosage schedule described above, the treatment regimen can continue indefinitely or until no further improvement is observed. Alternately, the treatment regimen can last for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 60 days, 70 days, 80 days, 90 days, 100 days, 150 days, 200 days, 250 days, 300 days, 400 days, 500 days, 750 days, 1000 days or more than 1000 days.

Devices

Some embodiments of the invention relate to devices for administering compositions comprising tylosin or a pharmaceutically acceptable salt thereof and a carrier suitable for ophthalmic application to a subject. In some embodiments, the devices include a reservoir that contains tylosin or a pharmaceutically acceptable salt thereof and a carrier suitable for ophthalmic application, and an applicator adapted to transfer the composition from the reservoir to the eye.

The applicator can be cylindrical, conical or any other shape which permits the compositions described herein to be delivered from the reservoir to the eye. In some embodiments, the reservoir is a tube and the applicator is a bulb. In some embodiments, the device for administering compositions comprising tylosin or a pharmaceutically acceptable salt thereof and a carrier suitable for ophthalmic application to a subject is an eye dropper.

In some embodiments, the devices contemplated herein comprise a container having a tip to facilitate drop formation in which the container stores tylosin or a pharmaceutically acceptable salt thereof and a carrier suitable for ophthalmic application. In some embodiments, the tip of such devices has a blunt end. In some embodiments, the tip is non-metallic and/or is not a needle. In various embodiments, the angle of the tip is greater than about 15 degrees.

While the present invention has been described in some detail for purposes of clarity and understanding, one skilled in the art will appreciate that various changes in form and detail can be made without departing from the true scope of the invention.

EXAMPLES

Having generally described embodiments drawn to compositions, methods, and devices useful for treating eye stain, a further understanding can be obtained by reference to certain specific examples which are provided herein for purposes of illustration only, and are not intended to be limiting.

Example 1

Preparation of a Pharmaceutical Composition Comprising Tylosin Tartrate

A pharmaceutical composition (Solution A) was prepared by dissolving 200 mg of tylosin tartrate and 2 mg of EDTA in 10 ml of sterile ophthalmic grade water. Solution A was provided in ophthalmic droppers. For comparison, a placebo control ophthalmic solution (Solution B) containing 10 ml of sterile ophthalmic grade water was provided in ophthalmic droppers.

Example 2

Reduction of Tear Production in Dogs Opthalmically Administered a Pharmaceutical Composition Comprising Tylosin Tartrate Two dogs having tear stain were selected for ophthalmic administration of Solution A of Example 1 and two dogs having tear stain were selected for ophthalmic administration of Solution B of Example 1. The dogs were chosen based on the following criteria.
Inclusion Criteria
 Excessive tear staining.
 Overproduction of tears.
 No gender bias.
 Age of 1-5 years.
Exclusion criteria
 Any ophthalmic infection
 Use of ophthalmic and/or oral steroids within the last 6 weeks
 Any active ophthalmic and/or oral diseases or uncontrolled systemic disease.
The dogs treated with Solution A received 6 drops in the eye daily and were evaluated for tear production each week by the Schirmer Tear Test (Intervet SPAH) (FIG. 3). Briefly, a Schirmer strip test was put inside the lower eyelid in the center of the eye and left there for 60 seconds. After the 60 seconds, which allowed the moisture of the eye to wet the paper, the length of the moistened area on the paper was measured. A moist length of 15 mm to 20 mm is considered normal, a moist length 11 mm to 14 mm is considered a borderline result, a moist length less than 10 mm is considered dry, and a moist length of less than 5 mm is considered severely dry. The results of the two dogs treated with Solution A are shown in Table 2 below:

TABLE 2

| Schirmer Tear Test Results (Solution A) | | |
|---|---|---|
| Day | Dog 1 (Schirmer Test Result) | Dog 2 (Schirmer Test Result) |
| Initial data | 26 | 29 |
| 7 | 23 | 27 |
| 14 | 21 | 24 |
| 21 | 18 | 21 |
| 28 | 17 | 18 |
| 35 | 17 | 18 |

Note:
All data were obtained from three measurements and presented as, mean +/− S.D.

Figure 4:
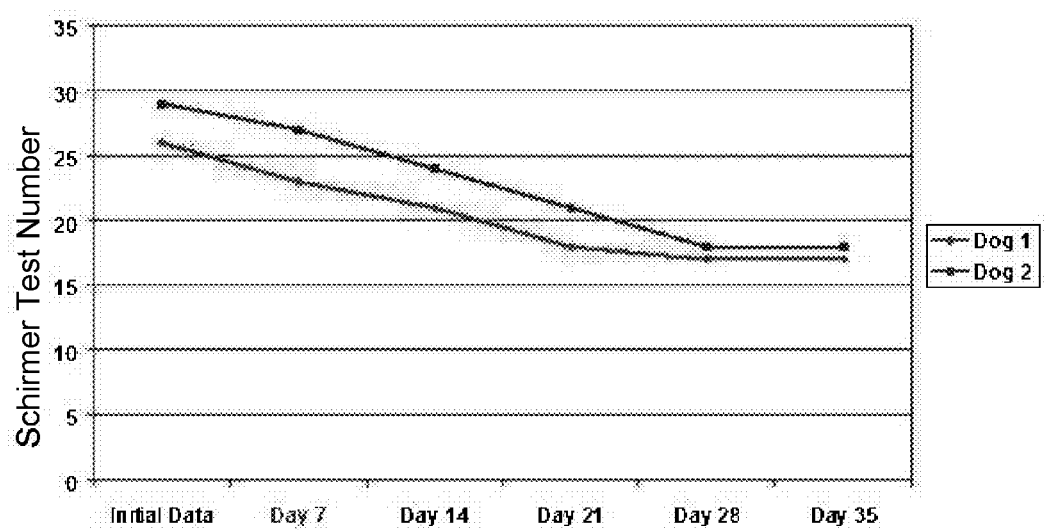
FIG. 4 is a graph plotting the Schirmer Test number of tear reduction over time in dogs administered an ophthalmic solution including tylosin.

The data presented in Table 2 clearly show the reduction in tear production in the two dogs when opthalmically given Solution A. A graphical presentation of the data shown in Table 2 is provided in FIG. 4. Additionally, the dogs did not show any side effects such as eye irritation, inflammation, infection, salivation or vomiting due to application of Solution A.

The dogs treated with placebo Solution B received 6 drops in the eye daily of the solution and were evaluated for tear production each week by the Schirmer Tear Test (Intervet SPAH) as described above. The results of the two dogs treated with placebo Solution B are shown in Table 3 below:

TABLE 3

| Schirmer Tear Test Results (Solution B) | | |
|---|---|---|
| Day | Dog 1 (Schirmer Test Result) | Dog 2 (Schirmer Test Result) |
| Initial data | 24 | 26 |
| 7 | 24 | 26 |
| 14 | 25 | 26 |
| 21 | 24 | 27 |
| 28 | 24 | 28 |
| 35 | 25 | 28 |

Note:
All data were obtained from three measurements and presented as, mean +/− S.D.

Figure 5:
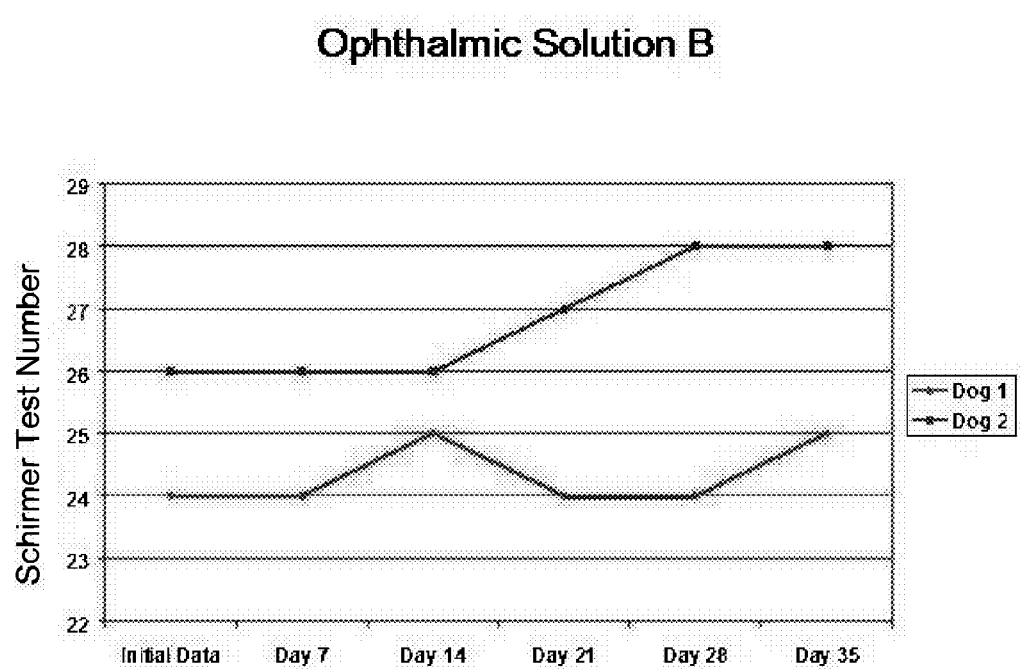
FIG. 5 is a graph plotting the shows the Schirmer Test number of tear reduction over time in dogs administered a placebo solution.

The data presented in Table 3 clearly show that the placebo (sterile water ophthalmic grade) does not have an effect on tear production. A graphical presentation of the data shown in Table 3 is provided in FIG. 5.

Example 3

Stain and Bad Breath Reduction in Dogs Opthalmically Administered a Pharmaceutical Composition Comprising Tylosin Tartrate Two dogs having tear stain were selected for ophthalmic administration of Solution A of Example 1 and two dogs having tear stain were selected for ophthalmic administration of Solution B of Example 1. Before beginning the application of Solution A or Solution B, the two dogs were medically evaluated to verify that they did not have a confounding disorder such as ocular infection, ocular inflammation, stomach problems, diarrhea, or skin infections.

Figure 6:
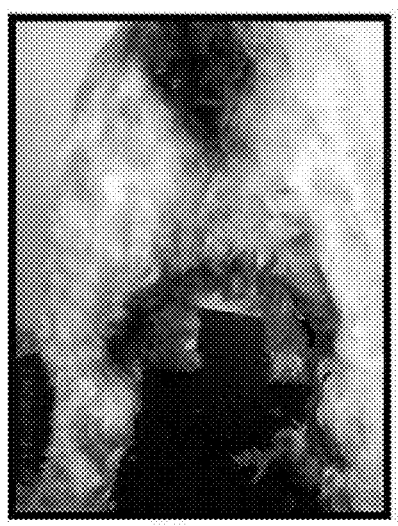
FIGS. 6A-6B are photographs of a dog having stain around its legs and anal region before (6A) and after (6B) being administered a solution containing tylosin directly to the eye for 30 days.
FIGS. 6C-6D are photographs of a dog having eye stain before (6C) and after (6D) being administered with an ophthalmic solution containing tylosin for 30 days.
Figure 6:
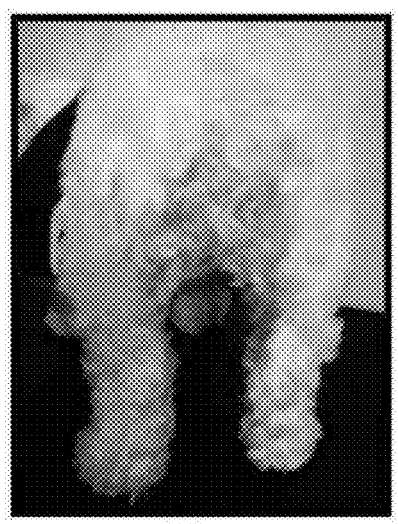
Figure 6:
Figure 6:

The two dogs selected for ophthalmic administration of Solution A had bad breath, excessive tearing, and a bad odor around the eye area. The two dogs received 4 drops of Solution A daily for 30 days. As shown in FIG. 6, ophthalmic administration of Solution A eliminated the stains around the eyes, mouth, genitals, and legs. Additionally, Solution A removed bad breath within 10 days of administration.

Figure 7:
FIGS. 7A-7B are photographs of a dog having eye stain before (7A) and after (7B) being administered with a placebo solution for 30 days.
Figure 7:

The two dogs selected for ophthalmic administration of Solution B had bad breath, excessive tearing, and a bad odor around the eye area. The two dogs received 4 drops of Solution B daily for 30 days. As shown in FIG. 7, ophthalmic administration of Solution B did not remove the hair stain under the eyes. Additionally, Solution B did not remove bad breath or the odor around the eyes after 30 days of application.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

What is claimed is:

1. A method of reducing eye stain in a subject comprising:
   identifying an animal in need of treatment for eye stain, and
   topically administering a composition comprising a therapeutically effective amount of tylosin or a pharmaceutically acceptable salt thereof to the eye of the animal, wherein the administration of the composition reduces eye stain.

2. The method of claim 1, wherein administration of the composition is effective to reduce bacterial or yeast infection of the eye, thereby reducing the eye stain.

3. The method of claim 2, wherein the bacterial infection is a Ptyrosporin infection.

4. The method of claim 2, wherein the yeast infection is a Red Yeast infection.

5. The method of claim 1, wherein the pharmaceutically acceptable salt is tylosin tartrate.

6. The method of claim 5, wherein the tylosin is present at a concentration from about 0.1 mg/ml to about 50 mg/ml.

7. The method of claim 1, wherein the composition further comprises an ophthalmic demulcent, and a carrier suitable for ophthalmic application.

8. The method of claim 7, wherein the demulcent is selected from the group consisting of carboxymethylcellulose, hydroxyethylcellulose, hypromellose, methylcellulose, dextran, gelatin, glycerin, polyethylene glycol, polysorbate, propylene glycol, polyvinyl alcohol, and providone.

9. The method of claim 7, wherein said carrier suitable for ophthalmic application is a solution comprising an isotonic agent.

10. The method of claim 7, wherein said carrier suitable for ophthalmic application is a plurality of microspheres, each microsphere comprising:
    a core comprising the tylosin; and
    a bioadhesive coat.

11. The method of claim 7, wherein the composition further comprises a preservative.

12. The method of claim 7, wherein the tylosin is present at a concentration from about 0.1 mg/ml to about 50 mg/ml.

13. The method of claim 1, wherein the tylosin is present at a concentration from about 0.1 mg/ml to about 50 mg/ml.

14. The method of claim 1, wherein the composition comprises:
    about 0.1 mg/ml to about 500 mg/ml tylosin tartrate, glycerin, polyethylene glycol, ethylene-diamine-tetra-acetic acid, sodium chloride and benzalkonium chloride.

15. The method of claim 14, wherein the composition comprises:
    about 50 mg/ml tylosin tartrate.

16. The method of claim 1, wherein the animal is a cat or dog.

* * * * *